United States Patent [19]

Crespi

[11] Patent Number: 5,016,477
[45] Date of Patent: May 21, 1991

[54] APPARATUS FOR MEASURING THE FLEXURAL RESISTANCE OF RIBBED PATTERNS

[76] Inventor: Giuseppe Crespi, Corso Novara, 225 - 27029 Vigevano (Pavia), Italy

[21] Appl. No.: 471,275

[22] Filed: Jan. 26, 1990

[30] Foreign Application Priority Data

Feb. 2, 1989 [IT] Italy ................................ 19296 A/89

[51] Int. Cl.[5] ............................................. G01N 3/20
[52] U.S. Cl. ...................................................... 73/849
[58] Field of Search .................. 73/849, 850, 851, 812

[56] References Cited

U.S. PATENT DOCUMENTS 4,358,962 11/1982 Ashby et al. ........................... 73/849
4,753,113 6/1988 Lumsden ............................... 73/849

Primary Examiner—Jerry W. Myracle
Attorney, Agent, or Firm—Bucknam and Archer

[57] ABSTRACT

An apparatus for measuring the flexural resistance of ribberd patterns comprises a clamp for clamping a die-cut and ribbed cardboard sheet, which clamp is so driven as to cause the ribbed portions of the cardboard sheet to engage against one or more rollers which are coupled to corresponding load cells adapted to measure the force necessary for folding the ribbed portions and display this force on a display.

6 Claims, 2 Drawing Sheets

5,016,477

APPARATUS FOR MEASURING THE FLEXURAL RESISTANCE OF RIBBED PATTERNS

BACKGROUND OF THE INVENTION

The present invention relates to an apparatus for measuring instantaneously the flexural resistance of ribbed patterns or elements, in particular cardboard ribbed elements.

As is known for packaging purposes there are frequently used cardboard sheets which are provided with ribbed patterns on their surface and are die-cut so as to provide a box-like configuration adapted to hold a lot of different products.

At present there are not known means for instantaneously measuring, in a reliable way, the proper characteristics of ribbed cardboard sheets to be used for packaging goods, in industrial packaging operations.

Known flexural resistance measuring devices, in fact, are mainly of the laboratory type, and are very complex and expensive.

SUMMARY OF THE INVENTION

Thus, the main object of the present invention is to overcome the above mentioned drawbacks, by providing an apparatus which able of measuring the flexural resistance of ribbed cardboard sheet material, in particular for packaging purposes, in a very short time.

Another object of the present invention is to provide such a flexural resistance measuring apparatus which is very simple to use.

Another object of the present invention is to provide such a flexural measuring apparatus which is very reliable in operation and can be used directly on the cardboard sheet making line.

According to one aspect of the present invention, the above mentioned objects, as well as yet other objects, which will become more apparent hereinafter, are achieved by an apparatus for instantaneously measuring flexural resistance of ribbed cardboard sheet material, characterized in that said apparatus comprises a clamp member for clamping a ribbed cardboard sheet material, driving means for driving said clamp member so as to cause ribbed portions of said ribbed cardboard sheet material to be engaged against one or more rollers, said rollers being associated with respective load cells adapted to measure the force required for bending said ribbed portions and display said force on display means.

BRIEF DESCRIPTION OF THE DRAWINGS

Further characteristics and advantages of the apparatus according to the present invention will become more apparent from the following detailed disclosure of a preferred embodiment thereof, which is illustrated, by way of an indicative but not limitative example, in the figures of the accompanying drawings, where.

DESCRIPTION OF THE PREFERRED EMBODIMENT

Figure 1:
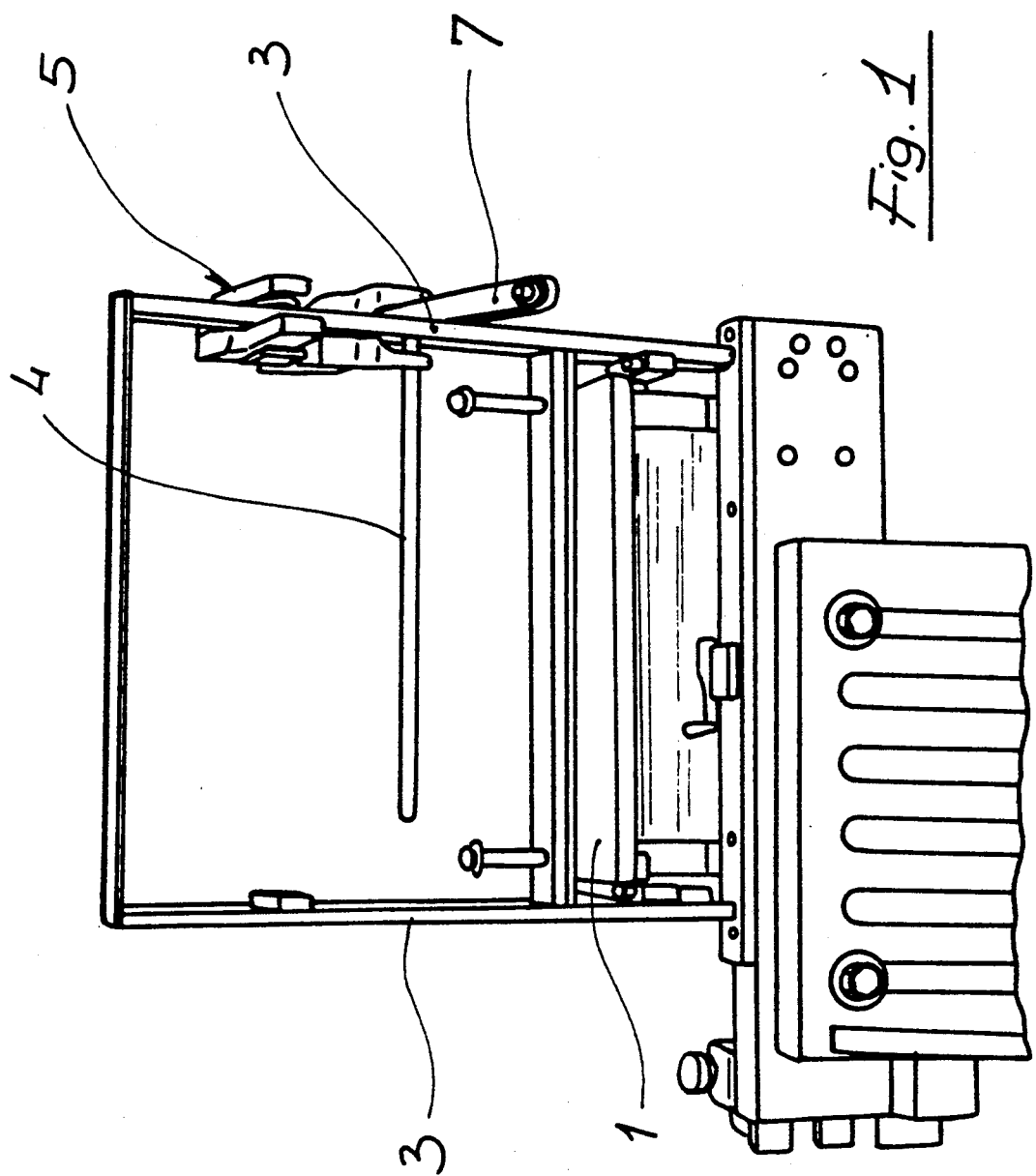
FIG. 1 is an elevation schematic view of the apparatus according to the invention.
Figure 2:
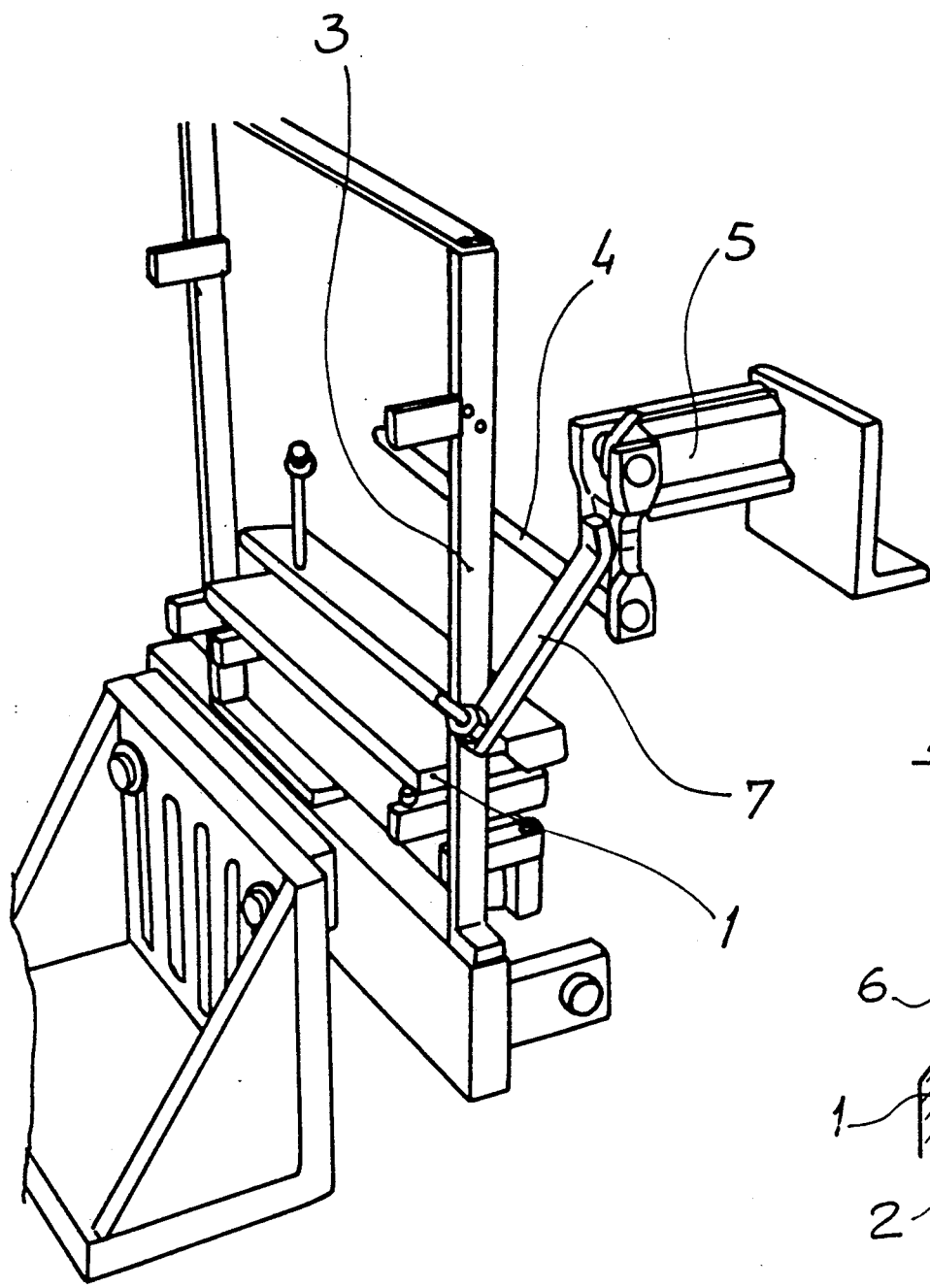
FIG. 2 is a side perspective view of the apparatus according to the invention.
Figure 3:
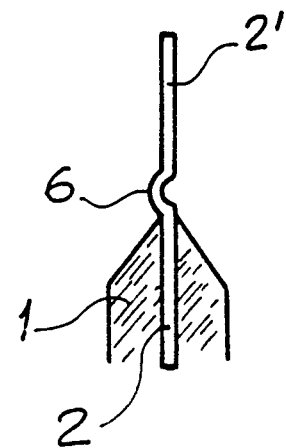
FIGS. 3 and 4 illustrate the operating mode of the apparatus.

With reference to the figures of the accompanying drawings, the apparatus for instantaneously measuring the flexural resistance of ribbed patterns, in particular on cardboard sheet material, according to the invention, comprises essentially a clamp member indicated overally at the reference number 1 and comprising a pair of flat plates which can be mutually clamped in any suitable manner, for example by means of actuators driven by suitable sensors (not shown).

The plates are provided for clamping therebetween a cardboard sheet 2, provided for forming, upon folding, a desired packaging box or the like.

As is shown, the mentioned pair of plates can slide between the uprights 3 of a frame, said plates being horizontally reciprocated by driving means.

These driving means can comprise any suitable driving arrangement. According to a possible embodiment, for example, the clamp member can be mounted on small columns or rods rigid with suitable guides and provided with a rack shaped bottom portion engaging with a pignon, which is driven by a geared motor unit (not shown).

In operation, the clamp member is upwardly driven so as to cause the ribbed portion 2' of the cardboard sheet to engage with one or more rollers 4 which are suitable coupled to respective load cells 5.

As is known, the flexural resistance of a ribbed portion or pattern 6 to a bending stress, comprising a 90° folding of the ribbed portion so as to form the packaging box, increases as the bending angle increases and reaches a maximum value for a bending angle of 90°.

Figure 4:
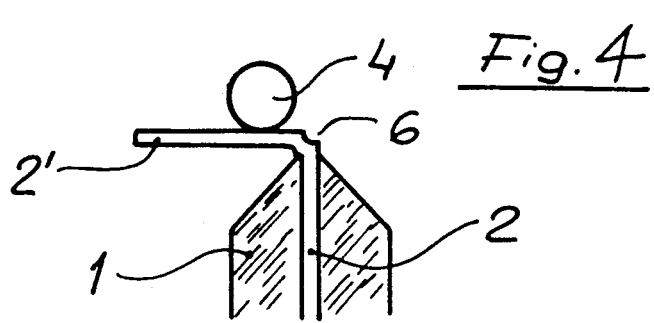

Thus, according to the invention, the clamp member and roller are so arranged that the portion 2' of the cardboard will be deflected according to a right angle bend before the clamp member going beyond the roller (see FIG. 4).

The flexural resistance of the mentioned portion 2' will be sensed by the above mentioned load cell, the output signal of which, after suitable amplification and conversion, will drive any suitable display means.

In this connection it should be pointed out that a repeated measurement on the same fold will provide progressively decreasing read-outs.

Thus, by storing the subsequent flexural resistance values in a pre-programmed computer store, and using a roller which can be displaced by set distances along its axis, it will be possible to evaluate the flexural resistance of two or more adjoining ribbed portions.

In particular, the roller must be counterbiassed, for example by means of a radial arm 7, in order to cancel the weight of said roller (which, on the other hand can also be electronically cleared by a suitable calibrating procedure.

Moreover the roller must be mounted on bearings in order to prevent the measurement readouts to be negatively affected by a possible unevenness of the ribbed portion surface.

It is to be moreover pointed out that:

the roller will be coupled to the load cell preferably by means of a rigid type of coupling, in order to hold said roller at a fixed position;

the position of the roller with respect to the clamp member, and accordingly to the fold, must not be affected by the thickness of the cardboard sheet.

While the invention has been disclosed and illustrated with reference to a preferred embodiment thereof, it should be apparent that the disclosed embodiment is susceptible to several modifications and variations, all of which will come within the spirit and scope of the appended claims.

I claim:

1. An apparatus for instantaneously measuring a flexural resistance characteristic of a ribbed cardboard sheet, comprising a frame including two parallel uprights, a clamp member for clamping a ribbed cardboard sheet, said clamp member being slidably supported on said uprights and comprising a pair of flat sliding plates which can be abutted against one another and are slidably mounted between said parallel uprights, driving means for upward and downward driving said clamp member, at least a roller thereagainst a ribbed portion of said cardboard sheet can be engaged as said driving means upward drive said clamp member, a load cell coupled to said at least a roller and adapted to measure a force required for folding said ribbed portion and display means for displaying said force.

2. An apparatus according to claim 1, wherein said clamp member and roller are so arranged that said ribbed portion of said cardboard sheet assumes a 90° bent configuration before said clamp member goes beyond said roller.

3. An apparatus according to claim 1, wherein said at least a roller can translate along a longitudinal axis thereof.

4. An apparatus according to claim 1, wherein said at least a roller is counterbiassed by a radial arm member.

5. An apparatus according to claim 1, wherein said at least a roller is mounted on bearing means.

6. An apparatus according to claim 1, wherein said at least a roller is rigidly coupled to said load cell.

* * * * *